(12) United States Patent     (10) Patent No.:   US 12,687,470 B2

Alshaiba Saleh Ghannam Almazrouei et al. (45) Date of Patent:    Jul. 21, 2026

---

(54) CELL LYSIS SYSTEMS AND METHODS

(71) Applicant: SHAHEEN INNOVATIONS HOLDING LIMITED, Abu Dhabi (AE)

(72) Inventors: Mohammed Alshaiba Saleh Ghannam Almazrouei, Abu Dhabi (AE); Sajid Bhatti, Abu Dhabi (AE); Jeffrey Machovec, Abu Dhabi (AE); Clement Lamoureux, Abu Dhabi (AE); Imad Lahoud, Abu Dhabi (AE)

(73) Assignee: SHAHEEN INNOVATIONS HOLDING LIMITED, Abu Dhabi (AE)

( * ) Notice: Subject to any disclaimer, the term of this patent is extended or adjusted under 35 U.S.C. 154(b) by 1199 days.

(21) Appl. No.: 17/220,224

(22) Filed: Apr. 1, 2021

(65) Prior Publication Data

US 2021/0310913 A1     Oct. 7, 2021

Related U.S. Application Data

(63) Continuation-in-part of application No. 17/122,025, filed on Dec. 15, 2020, now Pat. No. 11,672,928, and (Continued)

(30) Foreign Application Priority Data

Apr. 6, 2020    (EP) ..................................... 20168245

(51) Int. Cl.
   *G01N 1/40*      (2006.01)
   *B01L 3/00*      (2006.01)
       (Continued)

(52) U.S. Cl.
   CPC .............. *G01N 1/4044* (2013.01); *B01L 3/50* (2013.01); *C12Q 1/6806* (2013.01); *G01N 1/31* (2013.01);
       (Continued)

(58) Field of Classification Search
   CPC ........ G01N 1/4044; G01N 1/31; G01N 29/00; G01N 29/34; G01N 2001/4094;
       (Continued)

(56) References Cited

U.S. PATENT DOCUMENTS 4,864,547 A *   9/1989   Krsna ................... B06B 1/0223
                                 310/317
4,874,137 A *   10/1989   Chiba .................... C12N 1/066
                                  241/1

(Continued)

FOREIGN PATENT DOCUMENTS

CN      101648041 A    2/2010
CN      104055225 A    9/2014
(Continued)

OTHER PUBLICATIONS

Lim, H. J., et al. "Portable lysis apparatus for rapid singleăstep DNA extraction of Bacillus subtilis." Journal of Applied Microbiology 120.2 (2016): 379-387. (Year: 2016).*

(Continued)

*Primary Examiner* — James Lin
*Assistant Examiner* — John Lee
(74) *Attorney, Agent, or Firm* — Amedeo F. Ferraro, Esq.

(57)          ABSTRACT

A cell lysis system (1) comprises a driver apparatus (2) and a cell lysis device (3) which are releasably attachable to one another. The cell lysis device (3) comprises an ultrasonic transducer (12) and a sonication chamber (11). The driver apparatus (2) drives the ultrasonic transducer (12) to output
(Continued)

ultrasonic waves to lyse cells in a sample container (22) which is carried by the cell lysis device (3).

13 Claims, 8 Drawing Sheets

Related U.S. Application Data a continuation-in-part of application No. 17/065,992, filed on Oct. 8, 2020, now abandoned, and a continuation-in-part of application No. 16/889,667, filed on Jun. 1, 2020, now Pat. No. 11,254,979.

(60) Provisional application No. 63/111,592, filed on Nov. 9, 2020.

(51) Int. Cl.

| | |
|---|---|
| *C12Q 1/6806* | (2018.01) |
| *G01N 1/31* | (2006.01) |
| *G01N 29/00* | (2006.01) |
| *G01N 29/34* | (2006.01) |

(52) U.S. Cl.
CPC ............. *G01N 29/00* (2013.01); *G01N 29/34* (2013.01); *B01L 2400/0439* (2013.01)

(58) Field of Classification Search
CPC ... G01N 29/02; B01L 3/50; B01L 2400/0439; C12Q 1/6806; C12N 13/00; C12N 1/066; C12M 47/06; B06B 1/0253; B06B 1/0261
USPC ..................................................... 204/157.62
See application file for complete search history.

(56) References Cited

U.S. PATENT DOCUMENTS

| | | | | |
|---|---|---|---|---|
| 4,888,565 | A * | 12/1989 | Littleford | ................ H03L 7/183 |
| | | | | 331/25 |
| 5,406,503 | A * | 4/1995 | Williams, Jr. | ........ B06B 1/0253 |
| | | | | 73/579 |
| 5,518,179 | A | 5/1996 | Humberstone et al. | |
| 5,777,860 | A * | 7/1998 | Halbert | ................. B06B 1/0253 |
| | | | | 310/317 |
| 5,894,841 | A | 4/1999 | Voges | |
| 5,895,997 | A * | 4/1999 | Puskas | ................. B06B 1/0284 |
| | | | | 134/1 |
| 6,040,560 | A | 3/2000 | Fleischhauer | |
| 6,100,084 | A | 8/2000 | Miles | |
| 6,374,684 | B1 | 4/2002 | Dority | |
| 6,402,046 | B1 | 6/2002 | Loeser | |
| 6,440,725 | B1 | 8/2002 | Pourahmadi | |
| 6,601,581 | B1 | 8/2003 | Babaev | |
| 6,660,228 | B1 | 12/2003 | Chang | |
| 6,679,436 | B1 | 1/2004 | Onishi | |
| 6,686,195 | B1 | 2/2004 | Colin | |
| 6,819,027 | B2 * | 11/2004 | Saraf | ..................... B06B 1/0261 |
| | | | | 310/316.01 |
| 6,878,540 | B2 | 4/2005 | Pourahmadi | |
| 6,881,541 | B2 | 4/2005 | Peterson | |
| 7,129,619 | B2 | 10/2006 | Yang | |
| 7,247,274 | B1 | 7/2007 | Chow | |
| 7,279,146 | B2 | 10/2007 | Nassef | |
| 7,538,473 | B2 * | 5/2009 | Blandino | ............. H10N 30/802 |
| | | | | 310/317 |
| 8,169,122 | B1 | 5/2012 | Roberts | |
| 8,221,700 | B2 | 7/2012 | Steinmiller | |
| 8,222,049 | B2 | 7/2012 | Linder | |
| 8,591,829 | B2 | 11/2013 | Taylor | |
| 8,815,521 | B2 | 8/2014 | Taylor | |
| 8,906,624 | B2 | 12/2014 | Seo | |
| 8,991,722 | B2 | 3/2015 | Friend | |
| 9,052,275 | B2 | 6/2015 | Khattak | |
| 9,278,365 | B2 | 3/2016 | Banco | |

| | | | | |
|---|---|---|---|---|
| 9,415,412 | B2 | 8/2016 | Kawachima | |
| 9,580,745 | B2 | 2/2017 | Ermantraut | |
| 9,669,409 | B2 | 6/2017 | Dority | |
| 9,687,029 | B2 | 6/2017 | Liu | |
| 9,687,627 | B2 | 6/2017 | Gallem | |
| 9,718,078 | B1 | 8/2017 | Chau | |
| 9,789,481 | B2 | 10/2017 | Peterson | |
| 9,867,398 | B2 | 1/2018 | Guo | |
| 9,943,848 | B2 | 4/2018 | Taylor | |
| 10,034,495 | B2 | 7/2018 | Alarcon | |
| 10,067,487 | B2 * | 9/2018 | Tierce | ................... B06B 1/0207 |
| 10,071,391 | B2 | 9/2018 | Yu | |
| 10,195,368 | B2 | 2/2019 | Wang | |
| 10,300,225 | B2 | 5/2019 | Terry | |
| 10,327,736 | B1 * | 6/2019 | Puskas | ................. B06B 1/0662 |
| 10,328,218 | B2 | 6/2019 | Reed | |
| 10,378,045 | B2 | 8/2019 | Connolly | |
| 10,556,132 | B2 * | 2/2020 | Tyler | .................... C12N 5/0619 |
| 10,561,803 | B2 | 2/2020 | Liu | |
| 10,562,030 | B2 | 2/2020 | Dority | |
| 2002/0042125 | A1 * | 4/2002 | Petersen | ................ C12M 47/02 |
| | | | | 436/178 |
| 2002/0081669 | A1 | 6/2002 | Festoc | |
| 2002/0129813 | A1 | 9/2002 | Litherland | |
| 2003/0209005 | A1 | 11/2003 | Fenn | |
| 2004/0042936 | A1 | 3/2004 | Ido | |
| 2004/0099218 | A1 | 5/2004 | Yang | |
| 2004/0200909 | A1 | 10/2004 | McMillan | |
| 2004/0224325 | A1 | 11/2004 | Knapp | |
| 2004/0265393 | A1 * | 12/2004 | Unger | ................ A61K 41/0028 |
| | | | | 604/20 |
| 2005/0244837 | A1 | 11/2005 | McMillan | |
| 2006/0030796 | A1 | 2/2006 | Xu | |
| 2006/0158956 | A1 | 7/2006 | Laugham, Jr. | |
| 2007/0016235 | A1 * | 1/2007 | Tanaka | ........... A61B 17/320092 |
| | | | | 606/169 |
| 2008/0088202 | A1 | 4/2008 | Duru | |
| 2008/0156320 | A1 | 7/2008 | Low | |
| 2008/0164339 | A1 | 7/2008 | Duru | |
| 2010/0139652 | A1 | 6/2010 | Lipp | |
| 2010/0159582 | A1 | 6/2010 | Ismail | |
| 2011/0063943 | A1 | 3/2011 | Chow | |
| 2011/0251527 | A1 | 10/2011 | Kushculey | |
| 2012/0009667 | A1 | 1/2012 | Peterson | |
| 2012/0126041 | A1 | 5/2012 | Mahito et al. | |
| 2014/0007864 | A1 | 1/2014 | Gordon | |
| 2014/0087359 | A1 | 3/2014 | Njoroge | |
| 2014/0186832 | A1 | 7/2014 | Fuchs | |
| 2015/0231347 | A1 | 8/2015 | Gumaste | |
| 2015/0292038 | A1 | 10/2015 | Seo | |
| 2015/0344868 | A1 | 12/2015 | Savage | |
| 2016/0001316 | A1 | 1/2016 | Friend | |
| 2016/0101421 | A1 * | 4/2016 | Ching | ..................... B01L 7/525 |
| | | | | 435/6.12 |
| 2016/0206001 | A1 | 7/2016 | Eng | |
| 2017/0135411 | A1 | 5/2017 | Cameron | |
| 2017/0265521 | A1 | 9/2017 | Do | |
| 2017/0303594 | A1 | 10/2017 | Cameron | |
| 2018/0042306 | A1 | 2/2018 | Atkins | |
| 2018/0153217 | A1 | 6/2018 | Liu | |
| 2018/0207551 | A1 | 7/2018 | Lipkens | |
| 2018/0310625 | A1 | 11/2018 | Alarcon | |
| 2018/0338532 | A1 | 11/2018 | Verleur | |
| 2018/0343926 | A1 | 12/2018 | Wensley | |
| 2019/0046989 | A1 | 2/2019 | Ririe | |
| 2019/0242917 | A1 | 8/2019 | Ogg | |
| 2019/0255554 | A1 | 8/2019 | Selby | |
| 2019/0289918 | A1 | 9/2019 | Hon | |
| 2019/0344269 | A1 | 11/2019 | Johnson | |
| 2019/0381498 | A1 | 12/2019 | Fruchter | |
| 2020/0009600 | A1 | 1/2020 | Tan | |
| 2020/0016344 | A1 | 1/2020 | Scheck | |
| 2021/0024877 | A1 | 1/2021 | Lockhart | |

FOREIGN PATENT DOCUMENTS

| | | |
|---|---|---|
| CN | 204070580 U | 1/2015 |
| CN | 105747277 A | 7/2016 |

(56) References Cited

FOREIGN PATENT DOCUMENTS

| CN | 105876873 | A | 8/2016 |
| CN | 205432145 | U | 8/2016 |
| CN | 106108118 | A | 11/2016 |
| CN | 205831074 | A | 12/2016 |
| CN | 106422005 | | 2/2017 |
| CN | 205947130 | U | 2/2017 |
| CN | 206025223 | U | 3/2017 |
| CN | 206043451 | U | 3/2017 |
| CN | 206079025 | U | 4/2017 |
| CN | 206119184 | U | 4/2017 |
| CN | 106617319 | A | 5/2017 |
| CN | 206303211 | U | 7/2017 |
| CN | 206333372 | U | 7/2017 |
| CN | 206586397 | U | 10/2017 |
| CN | 206949536 | U | 2/2018 |
| CN | 108283331 | A | 7/2018 |
| CN | 105747277 | B | 8/2018 |
| CN | 105876873 | B | 12/2018 |
| CN | 208434721 | U | 1/2019 |
| CN | 106108118 | B | 4/2019 |
| CN | 208837110 | U | 5/2019 |
| CN | 110150760 | A | 8/2019 |
| CN | 209255084 | U | 8/2019 |
| CN | 105876870 | B | 11/2019 |
| CN | 209900345 | U | 1/2020 |
| CN | 110946315 | A | 4/2020 |
| DE | 2656370 | A1 | 6/1978 |
| DE | 2656370 | B2 | 11/1978 |
| DE | 2656370 | C3 | 7/1979 |
| DE | 100 51 792 | A1 | 5/2002 |
| DE | 10122065 | A1 | 12/2002 |
| EP | 0186096 | | 7/1986 |
| EP | 0 258 637 | A1 | 3/1988 |
| EP | 0 295 122 | A2 | 12/1988 |
| EP | 0353365 | A2 | 2/1990 |
| EP | 0 258 637 | B1 | 6/1990 |
| EP | 0 442 510 | A1 | 8/1991 |
| EP | 0 516 565 | A1 | 12/1992 |
| EP | 0 442 510 | B1 | 1/1995 |
| EP | 0 516 565 | B1 | 4/1996 |
| EP | 0 845 220 | A1 | 3/1998 |
| EP | 0 833 695 | A1 | 4/1998 |
| EP | 0 893 071 | A1 | 1/1999 |
| EP | 0 824 927 | A | 2/1999 |
| EP | 0 970 627 | A1 | 1/2000 |
| EP | 1 179 585 | A2 | 2/2002 |
| EP | 1 083 952 | B1 | 12/2005 |
| EP | 1 618 803 | A1 | 1/2006 |
| EP | 1 618 803 | B1 | 12/2008 |
| EP | 3 088 007 | A1 | 11/2016 |
| EP | 3 192 381 | A1 | 7/2017 |
| EP | 3 278 678 | A1 | 2/2018 |
| EP | 3 298 912 | A1 | 3/2018 |
| EP | 3 088 007 | B1 | 11/2018 |
| EP | 3415199 | A1 * | 12/2018 | ............. A61B 18/12 |
| EP | 3 434 118 | A1 | 1/2019 |
| EP | 3 520 634 | A1 | 8/2019 |
| EP | 3 278 678 | B1 | 10/2019 |
| EP | 3 545 778 | A1 | 10/2019 |
| FR | 3043576 | A1 | 5/2017 |
| FR | 3064502 | A1 | 5/2018 |
| GB | 1 528 391 | A | 10/1978 |
| GB | 2 403 729 | A | 1/2005 |
| GB | 2566766 | A | 3/2019 |
| JP | 05093575 | U | 12/1993 |
| JP | 2579614 | Y2 | 8/1998 |
| JP | 2001069963 | A | 3/2001 |
| JP | 2005288400 | A | 10/2005 |
| JP | 2008-104966 | A | 5/2008 |
| JP | 2019-154404 | A | 9/2019 |
| KR | 10-2013-0095024 | | 8/2013 |
| WO | WO 92/21332 | A1 | 12/1992 |
| WO | WO9309881 | | 5/1993 |
| WO | WO 2000/050111 | A | 8/2000 |
| WO | WO 2002/055131 | A2 | 1/2003 |
| WO | WO 2003/055486 | A | 7/2003 |
| WO | WO 2003/0101454 | A | 12/2003 |
| WO | WO 2007/083088 | A1 | 7/2007 |
| WO | WO 2008/076717 | A1 | 6/2008 |
| WO | WO 2009/096346 | A1 | 8/2009 |
| WO | WO 2012/062600 | A1 | 5/2012 |
| WO | WO 2013/028934 | A1 | 2/2013 |
| WO | WO 2014/052671 | A1 | 4/2014 |
| WO | WO 2014/113543 | A1 | 7/2014 |
| WO | WO 2014/182736 | A1 | 11/2014 |
| WO | WO 2015/115006 | A1 | 8/2015 |
| WO | WO 2015/128499 | A1 | 9/2015 |
| WO | WO 2016/118941 | A1 | 7/2016 |
| WO | WO 2016/196915 | A1 | 12/2016 |
| WO | WO 2016/201385 | | 12/2016 |
| WO | WO 2017/076590 | A1 | 5/2017 |
| WO | WO 2017/079636 | A1 | 5/2017 |
| WO | WO 2017/143515 | A1 | 8/2017 |
| WO | WO 2017/177159 | A3 | 10/2017 |
| WO | WO 2017/206022 | A1 | 12/2017 |
| WO | WO 2018/041106 | A1 | 3/2018 |
| WO | WO 2018/113669 | A1 | 6/2018 |
| WO | WO 2018/211252 | A1 | 11/2018 |
| WO | WO 2018/220586 | A2 | 12/2018 |
| WO | WO 2019/048749 | A1 | 3/2019 |
| WO | WO 2019/069160 | A1 | 4/2019 |
| WO | WO 2019/130107 | A1 | 7/2019 |
| WO | WO 2019/138076 | A1 | 7/2019 |
| WO | WO 2020/019030 | A1 | 1/2020 |
| WO | WO 2021/036827 | A1 | 3/2021 |

OTHER PUBLICATIONS

Cintas, P., et al. "Glycerol: a solvent and a building block of choice for microwave and ultrasound irradiation procedures." Green Chemistry 16.3 (2014): 1056-1065. (Year: 2014).*

International Search Report and Written Opinion mailed Oct. 13, 2021 for International Appl. No. PCT/GB2021/050822.

Office Action Summary (Examination Result), Search Report, and Substantive Examination Result issued May 23, 2024 for co-pending UAE application No. P6002059/2022; 10 pages.

Examination Report No. 2 for co-pending AU application No. 2021252180 issued May 28, 2024; 5 pages.

Written Opinion mailed Nov. 10, 2020 for corresponding International Application No. PCT/IB2019/060812.

International Search Report mailed Nov. 10, 2020 for corresponding International Application No. PCT/IB2019/060812.

EPO Search Report mailed Nov. 9, 2020 for corresponding EPO Application No. 19870059.3 (PCT/IB2019/060808).

Written Opinion mailed Nov. 4, 2020 for corresponding International Application No. PCT/IB2019/060806.

International Search Report mailed Nov. 4, 2020 for corresponding International Application No. PCT/IB2019/060806.

Written Opinion mailed Nov. 4, 2020 for corresponding International Application No. PCT/IB2019/060807.

International Search Report mailed Nov. 4, 2020 for corresponding International Application No. PCT/IB2019/060807.

Written Opinion mailed Oct. 20, 2020 for corresponding International Application No. PCT/IB2019/060811.

International Search Report mailed Oct. 20, 2020 for corresponding International Application No. PCT/IB2019/060811.

Written Opinion mailed Oct. 19, 2020 for corresponding International Application No. PCT/IB2019/060810.

International Search Report mailed Oct. 19, 2020 for corresponding International Application No. PCT/IB2019/060810.

EPO Search Report dated Sep. 16, 2020 for corresponding EPO Application No. 20168231.

Extended EPO Search Report mailed Sep. 15, 2020 for corresponding EPO Application No. 20168938.7.

Written Opinion mailed Jun. 25, 2020 for corresponding International Application No. PCT/IB2019/060808.

International Search Report mailed Jun. 25, 2020 for corresponding International Application No. PCT/IB2019/060808.

(56)       References Cited

OTHER PUBLICATIONS

Written Opinion mailed Apr. 29, 2020 for corresponding International Application No. PCT/IB2019/055192.

International Search Report mailed Apr. 29, 2020 for corresponding International Application No. PCT/IB2019/055192.

EPO search report dated Sep. 20, 2017 for corresponding EPO Application No. 20168245.7.

Partial European Search Report for corresponding EPO Application No. 20177685.3 dated Nov. 17, 2020.

LabMate, Microchip RT-PCR COVID-19 Detection System Announced, avail at https://www.labmate-online.com/news/laboratory-products/3/limex-instruments/microchip-rt-pcr-covid-19-detection-system-announced/52084, published Apr. 25, 2020.

Zhang et al., (A new automatic resonance frequency tracking method for piezoelectric ultrasonic transducers used in thermosonic wire bonding, Nov. 2015 Sensors and Actuators A Physical 235:140-150).

Chen et al., Wirelessly addressable heater array for centrifugal microfluids and *Escherichia coli* sterilization, Annu Int Conf IEEE Eng Med Biol Soc. 2013; 2013:5505-8. doi: 10. 1109/EMBC.2013. 6610796.

European Search Report mailed Feb. 16, 2021 for corresponding EPO Application No. 20177685.3.

Cao et al., Plastic microfluidic chip for continuous-flow polymerase chain reaction: simulations and experiments, doi: 10.1002/biot. 201000100. Epub Nov. 4, 2010.

Li et al., A Continuous-Flow Polymerase Chain Reaction Microchip With Regional Velocity Control, J Microelectromech Syst. Feb. 1, 2006; 15(1 ): 223-236.

Thomas et al., Thermal gradient continuous-flow PCR: a guide to design, Dec. 2014 Microfluidics and Nanofluidics 17(6): 1039-1051 DOI: 10.1007/s 10404-014-1401-3.

UKIPO Invitation to Pay Additional Fees and, Where Applicable, Protest Fee for corresponding PCT application No. PCT/GB2021/050822, mailed Jul. 1, 2021.

International Search Report and Written Opinion for International Appl. No. PCT/GB2021/050842 mailed Jul. 5, 2021.

UKIPO Search Report for UK Appl. No. GB2104872.3 dated Jun. 25, 2021.

EPO Search Report and Search Opinion for International Appl. No. PCT/IB2019/060812 dated Jun. 22, 2021.

Extended European Search Report and Search Opinion for corresponding EP Application No. 20214228.7 dated May 26, 2021.

International Search Report for corresponding PCT Application No. PCT/GB2020/053219 mailed Mar. 31, 2021.

EPO Supplementary Search Report for EPO Application No. EP 3 278 678 A4 dated Oct. 4, 2018.

International Search Report for International Appl. No. WO 2017/177159 A3 mailed Sep. 26, 2017.

EPO Supplementary Search Report for EPO Application No. EP 1 618 803 A4 dated Jul. 27, 2007.

European Search Report issued Mar. 6, 2023, 7 pages, for co-pending European Application No. 22207045.0.

Yuan et al., Driving an Inductive Piezoelectric Transducer with Class E Inverter, Sensors and Actuators A: Physical, vol. 261, Jul. 1, 2017, pp. 219-227.

European Search Report for corresponding EPO Application No. E34854EP dated Mar. 26, 2021 (in English).

International Search Report and Written Opinion mailed Sep. 20, 2021 for International Appl. No. PCT/GB2021/051332.

International Search Report and Written Opinion mailed Sep. 20, 2021 for International Appl. No. PCT/GB2021/051333.

Marentis T.C. et al: "Microfluidic Sonicator for Real-Time Disruption of Eukaryotic Cells and Bacterial Spores for DNA Analysis", Ultrasound in Medicine Biology, New York, NY, US, vol. 31, No. 9, Sep. 1, 2005, pp. 1265-1277, XP027605632, ISSN: 0301-5629 [retrieved on Sep. 1, 2005], p. 1266-p. 1267.

Warner, C.L. et al.: "A Flow-Through Ultrasonic Lysis Module for the Disruption of Bacterial Spores", Journal of the Association for Laboratory Automation, Elsevier, vol. 14, No. 5, Oct. 1, 2009, pp. 277-284, XP026565091, ISSN: 1535-5535, DOI: 10.1016/J. Jala. 2009.04-007 [retrieved on Sep. 3, 2009] pp. 277, 278, p. 281-p. 283.

Examination Report No. 1 for AU application No. 2024210998 dated Mar. 31, 2025; 3 pages.

Official action for KR application No. 10-2022-7038658 dated Feb. 4, 2025; 7 pages (no translation available).

* cited by examiner

| Operating mode | First predetermined length of time (seconds) | Second predetermined length of time (seconds) |
|---|---|---|
| 1 | 4 | 2 |
| 2 | 3 | 2 |
| 3 | 2 | 2 |
| 4 | 1 | 2 |
| 5 | 1 | 1 |
| 6 | 2 | 1 |
| 7 | 3 | 1 |
| 8 | 4 | 1 |
| 9 | 4 | 3 |
| 10 | 3 | 3 |
| 11 | 2 | 3 |
| 12 | 1 | 3 |

*FIG. 9*

CELL LYSIS SYSTEMS AND METHODS

CROSS REFERENCES TO RELATED APPLICATIONS

The present application claims the benefit of priority to and incorporates by reference herein the entirety of each of: European patent application no. 20168245.7, filed on 6 Apr. 2020; U.S. patent application Ser. No. 16/889,667, filed on 1 Jun. 2020; U.S. patent application Ser. No. 17/065,992, filed on 8 Oct. 2020; U.S. provisional patent application No. 63/111,592, filed on 9 Nov. 2020; and U.S. patent application Ser. No. 17/122,025, filed on 15 Dec. 2020.

FIELD

The present invention relates to cell lysis systems and methods. The present invention more particularly relates to cell lysis systems and methods which use ultrasonic waves to lyse cells.

BACKGROUND

Polymerase Chain Reaction (PCR) is a process that uses the two matching strands in DNA to amplify a targeted DNA sequence from a small number of samples to billions of copies for analysis.

An initial step of the PCR process involves cell lysis to break or rupture the lipid bilayer of cells in a sample in order to provide a gateway through which a cell's components, including DNA and/or RNA, may be extracted. Cell lysis is typically performed either chemically or electromechanically, or a combination of both.

The cell lysis process extracts components from the cells in a liquid solution. The solution is then filtered to separate the nucleic acids (DNA/RNA) from other cell components. The extracted DNA/RNA can then be amplified and analysed in the remaining steps of the PCR process.

A conventional PCR apparatus performs cell lysis on a sample when the sample is input into the PCR apparatus. The components performing the cell lysis process are typically integrated within the PCR apparatus. The problem with a conventional PCR apparatus of this kind is that the apparatus is typically expensive and cumbersome. Moreover, the integrated components which perform the cell lysis are typically restricted for use only within the same PCR apparatus.

Standalone cell lysis devices have been proposed previously but these standalone devices can suffer from reduced efficiency and performance compared with the cell lysis functionality of a complete PCR apparatus.

Thus, a need exists in the art for improved cell lysis systems and methods which seek to address at least some of the problems described herein.

SUMMARY

According to some arrangements, there is provided a cell lysis system comprising: a driver apparatus which incorporates: a plurality of driver output terminals which provide an electrical connection between the driver apparatus and a cell lysis device to drive an ultrasonic transducer within the cell lysis device; an AC driver which generates an AC drive signal at a predetermined frequency and outputs the AC drive signal at the driver output terminals to drive the ultrasonic transducer within the cell lysis device; an active power monitoring arrangement which monitors the active power used by the ultrasonic transducer when the ultrasonic transducer is driven by the AC drive signal, wherein the active power monitoring arrangement provides a monitoring signal which is indicative of an active power used by the ultrasonic transducer; a processor which controls the AC driver and receives the monitoring signal from the active power monitoring arrangement; and a memory storing instructions which, when executed by the processor, cause the processor to:

A. control the AC driver to output an AC drive signal to the ultrasonic transducer at a predetermined sweep frequency;

B. calculate the active power being used by the ultrasonic transducer based on the monitoring signal;

C. control the AC driver to modulate the AC drive signal to maximise the active power being used by the ultrasonic transducer;

D. store a record in the memory of the maximum active power used by the ultrasonic transducer and the sweep frequency of the AC drive signal;

E. repeat steps A-D for a predetermined number of iterations with the sweep frequency incrementing with each iteration such that, after the predetermined number of iterations has occurred, the sweep frequency has been incremented from a start sweep frequency to an end sweep frequency;

F. identify from the records stored in the memory the optimum frequency for the AC drive signal which is the sweep frequency of the AC drive signal at which a maximum active power is used by the ultrasonic transducer; and G. control the AC driver to output an AC drive signal to the ultrasonic transducer at the optimum frequency.

In some arrangements, the active power monitoring arrangement comprises: a current sensing arrangement which senses a drive current of the AC drive signal driving the ultrasonic transducer, wherein the active power monitoring arrangement provides a monitoring signal which is indicative of the sensed drive current.

In some arrangements, the memory stores instructions which, when executed by the processor, cause the processor to: repeat steps A-D with the sweep frequency being incremented from a start sweep frequency of 2800 kHz to an end sweep frequency of 3200 kHz.

In some arrangements, the memory stores instructions which, when executed by the processor, cause the processor to: in step G, control the AC driver to output an AC drive signal to the ultrasonic transducer at frequency which is shifted by between 1-10% of the optimum frequency.

In some arrangements, the AC driver modulates the AC drive signal by pulse width modulation to maximise the active power being used by the ultrasonic transducer.

In some arrangements, the memory stores instructions which, when executed by the processor, cause the processor to: control the AC driver to alternately output an AC drive signal to the ultrasonic transducer at the optimum frequency for a first predetermined length of time and to not output an AC drive signal to the ultrasonic transducer for a second predetermined length of time.

In some arrangements, the memory stores instructions which, when executed by the processor, cause the processor to: alternately output the AC drive signal and to not output the AC drive signal according to an operating mode selected from:

| Operating mode | First predetermined length of time (seconds) | Second predetermined length of time seconds) |
|---|---|---|
| 1 | 4 | 2 |
| 2 | 3 | 2 |
| 3 | 2 | 2 |
| 4 | 1 | 2 |
| 5 | 1 | 1 |
| 6 | 2 | 1 |
| 7 | 3 | 1 |
| 8 | 4 | 1 |
| 9 | 4 | 3 |
| 10 | 3 | 3 |
| 11 | 2 | 3 |
| 12 | 1 | 3 |

In some arrangements, the system further comprises: a cell lysis device which is releasably attached to the driver apparatus, the cell lysis device comprising: a housing; a plurality of electrical terminals which are connected electrically to the plurality of driver output terminals; a sonication chamber provided within the housing, the sonication chamber being at least partly filled with an ultrasonic wave transfer medium, wherein the housing comprises an opening which is configured to receive a sample container such that a part of the sample container projects into the ultrasonic wave transfer medium; an ultrasonic transducer which generates ultrasonic waves in the ultrasonic wave transfer medium within the sonication chamber, wherein the ultrasonic waves are transferred by the ultrasonic wave transfer medium from the ultrasonic transducer to the sample container to lyse cells when cells are contained within the sample container.

In some arrangements, the driver apparatus comprises a first interference fit attachment and the cell lysis device comprises a second interference fit attachment, and wherein the first interference fit attachment releasably attaches to the second interference fit attachment to releasably attach the cell lysis device to the driver apparatus.

According to some arrangements, there is provided a cell lysis device comprising: a housing; a sonication chamber provided within the housing, the sonication chamber being at least partly filled with an ultrasonic wave transfer medium, wherein the housing comprises an opening which is configured to receive a sample container such that a part of the sample container projects into the ultrasonic wave transfer medium; an ultrasonic transducer which generates ultrasonic waves in the ultrasonic wave transfer medium within the sonication chamber, wherein the ultrasonic waves are transferred by the ultrasonic wave transfer medium from the ultrasonic transducer to the sample container to lyse cells when cells are contained within the sample container.

In some arrangements, the ultrasonic transducer is at least partly of a compound comprising lead, zirconium and titanium.

In some arrangements, the ultrasonic transducer is a circular disc shape and has a diameter of 16 mm and a thickness of 0.7 mm.

In some arrangements, the ultrasonic transducer comprises a first electrode and a second electrode which are provided on opposing sides of the ultrasonic transducer, wherein the first electrode and the second electrode comprise silver and the capacitance between the first electrode and the second electrode is 800 pF to 1300 pF.

In some arrangements, the first electrode is at least partly covered with a glass coating.

In some arrangements, the ultrasonic transducer is carried by a transducer holder which is of silicone rubber.

In some arrangements, the ultrasonic wave transfer medium comprises vegetable glycerine.

In some arrangements, the sample container is a microcentrifuge tube.

According to some arrangements, there is provided a method of lysing cells in a sample, the method comprising: placing a liquid sample containing cells to be lysed in a sample container; positioning the sample container through an opening in a housing of a cell lysis device such that a part of the sample container projects into an ultrasonic wave transfer medium provided in a sonication chamber within the housing; and attaching the cell lysis device to a driver apparatus, the driver apparatus incorporating: an AC driver which generates an AC drive signal at a predetermined frequency and outputs the AC drive signal at the driver output terminals to drive an ultrasonic transducer within the cell lysis device; an active power monitoring arrangement which monitors the active power used by the ultrasonic transducer when the ultrasonic transducer is driven by the AC drive signal, wherein the active power monitoring arrangement provides a monitoring signal which is indicative of an active power used by the ultrasonic transducer, wherein the method further comprises:

A. controlling, by a processor, the AC driver to output an AC drive signal to the ultrasonic transducer at a predetermined sweep frequency;

B. calculating, by the processor, the active power being used by the ultrasonic transducer based on the monitoring signal;

C. controlling, by the processor, the AC driver to modulate the AC drive signal to maximise the active power being used by the ultrasonic transducer;

D. storing a record in a memory of the maximum active power used by the ultrasonic transducer and the sweep frequency of the AC drive signal;

E. repeating steps A-D for a predetermined number of iterations with the sweep frequency incrementing with each iteration such that, after the predetermined number of iterations has occurred, the sweep frequency has been incremented from a start sweep frequency to an end sweep frequency;

F. identifying, by the processor, from the records stored in the memory the optimum frequency for the AC drive signal which is the sweep frequency of the AC drive signal at which a maximum active power is used by the ultrasonic transducer; and G. controlling, by the processor, the AC driver to output an AC drive signal to the ultrasonic transducer at the optimum frequency.

In some arrangements, the method further comprises: repeating steps A-D with the sweep frequency being incremented from a start sweep frequency of 2800 kHz to an end sweep frequency of 3200 kHz.

In some arrangements, the method further comprises: controlling, by the processor, the AC driver to alternately output an AC drive signal to the ultrasonic transducer at the optimum frequency for a first predetermined length of time and to not output an AC drive signal to the ultrasonic transducer for a second predetermined length of time.

BRIEF DESCRIPTION OF THE DRAWINGS

So that the present invention may be more readily understood, embodiments of the present invention will now be described, by way of example, with reference to the accompanying drawings, in which:

FIG. 9 is a table showing the timings of operating modes of a system of some arrangements.

DETAILED DESCRIPTION

Figure 1:
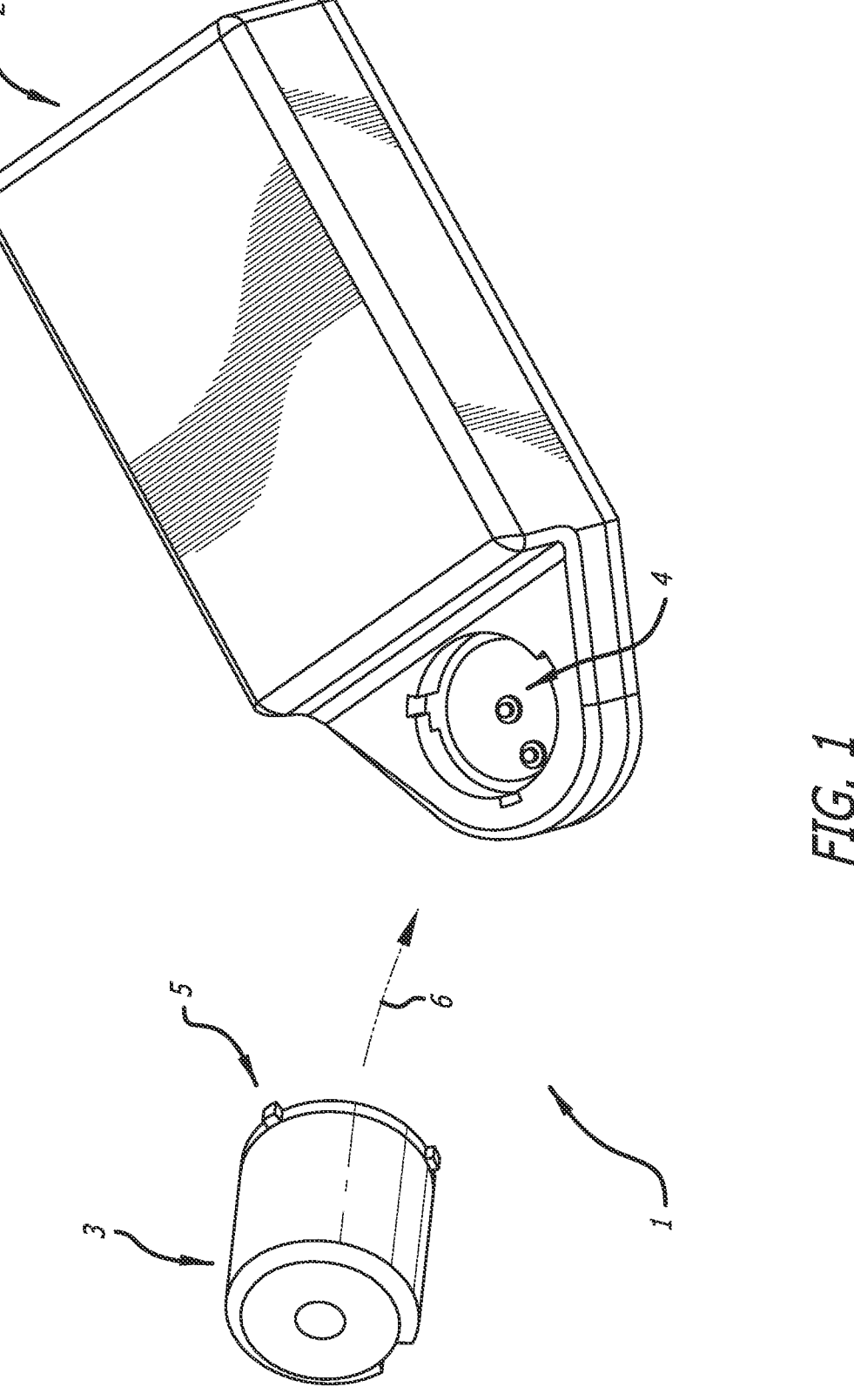
FIG. 1 is a diagrammatic perspective view of a system of some arrangements.

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

The following disclosure provides many different embodiments, or examples, for implementing different features of the provided subject matter. Specific examples of components, concentrations, applications and arrangements are described below to simplify the present disclosure. These are, of course, merely examples and are not intended to be limiting. For example, the attachment of a first feature and a second feature in the description that follows may include embodiments in which the first feature and the second feature are attached in direct contact, and may also include embodiments in which additional features may be positioned between the first feature and the second feature, such that the first feature and the second feature may not be in direct contact. In addition, the present disclosure may repeat reference numerals and/or letters in the various examples. This repetition is for the purpose of simplicity and clarity and does not in itself dictate a relationship between the various embodiments and/or configurations discussed.

The following disclosure describes representative arrangements or examples. Each example may be considered to be an embodiment and any reference to an "arrangement" or an "example" may be changed to "embodiment" in the present disclosure.

Referring initially to FIG. 1 of the accompanying drawings, a cell lysis system 1 of some arrangements comprises a driver apparatus 2 and a cell lysis device 3. The driver apparatus 2 comprises a first interference fit attachment 4 which releasably attaches to a second interference fit attachment 5 provided on the cell lysis device 3. The interference fit attachments 4, 5 allow the cell lysis device 3 to be releasably attached to the driver apparatus 2 when the cell lysis device 3 is placed onto the driver apparatus 2 as indicated generally by arrow 6 in FIG. 1.

The components of the cell lysis system 1 are described below, starting with the cell lysis device 3.

Figure 2:
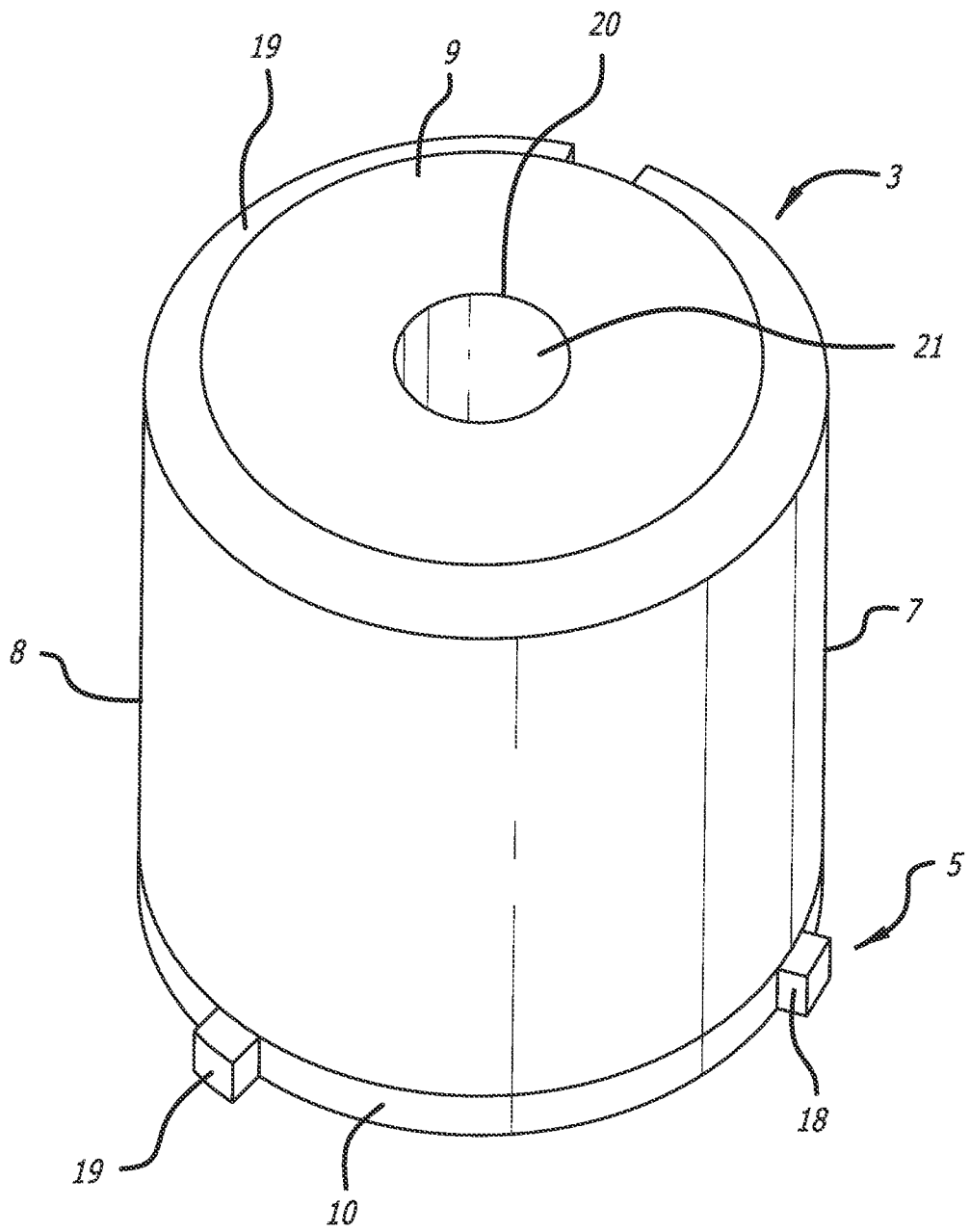
FIG. 2 is a diagrammatic perspective view of a cell lysis device of some arrangements.
Figure 3:
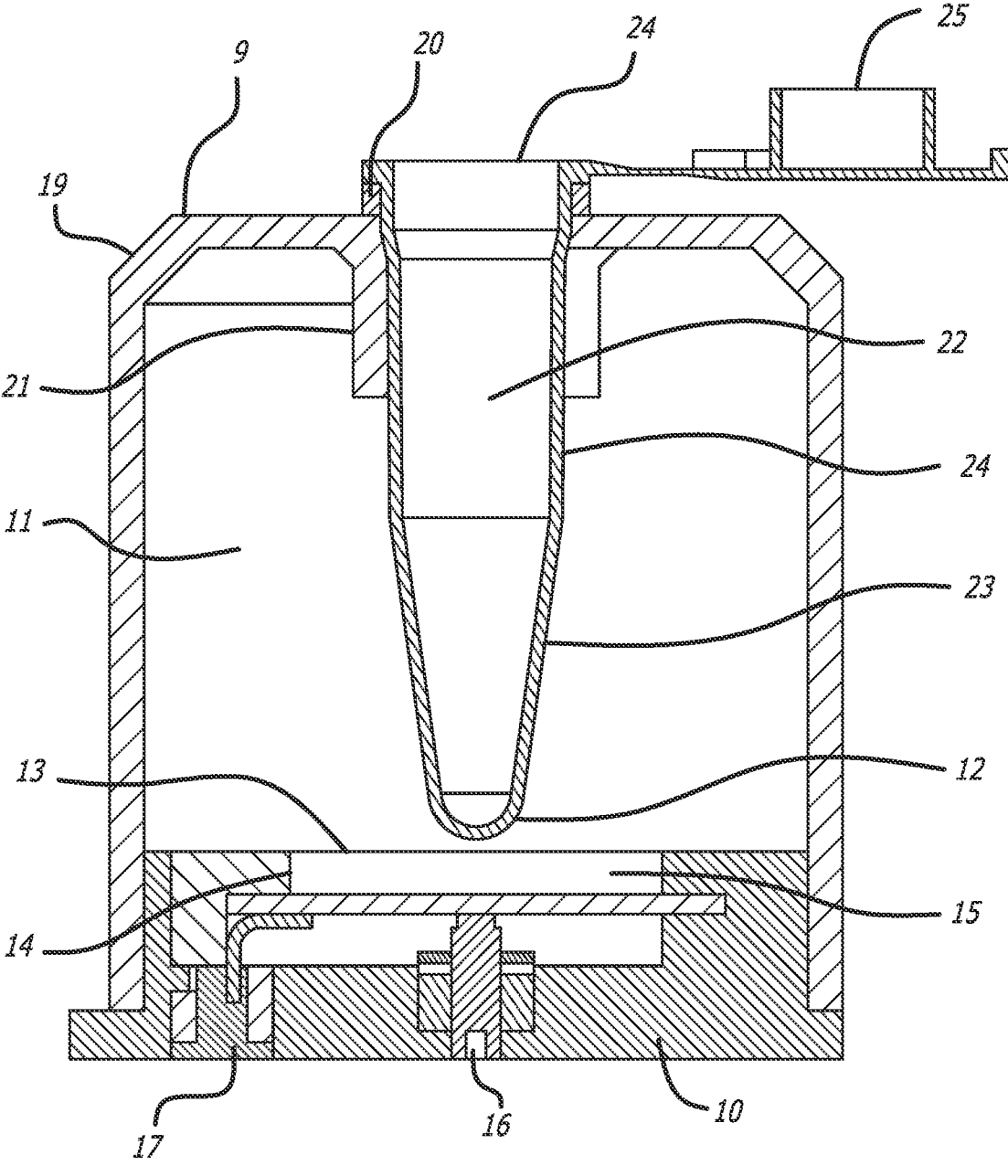
FIG. 3 is a cross-sectional view of the cell lysis device of FIG. 2.

Referring to FIGS. 2 and 3 of the accompanying drawings, the cell lysis device 3 of some arrangements comprises a housing 7. In this arrangement, the housing 7 is generally cylindrical with a side wall 8, a generally circular cover 9 at one end and a generally circular base 10 at the other end. In this arrangement, the cell lysis device 3 is a disposable, single-use capsule.

A sonication chamber 11 is provided within the housing 7. The sonication chamber 11 is at least partly filled with an ultrasonic wave transfer medium (not shown). In some arrangements, the sonication chamber 11 is pre-filled with the ultrasonic wave transfer medium. In other arrangements, the sonication chamber 11 is filled with an ultrasonic wave transfer medium when the cell lysis device is being prepared for use.

In some arrangements, the ultrasonic wave transfer medium is a liquid which has a higher acoustic impedance than water. In some arrangements, the ultrasonic wave transfer medium is vegetable glycerine since vegetable glycerine has a higher acoustic impedance than water.

The cell lysis device 3 comprises an ultrasonic transducer 12. An upper surface 13 of the ultrasonic transducer 12 faces towards the sonication chamber 11 so that ultrasonic waves generated by the ultrasonic transducer 12 are directed towards the sonication chamber 11.

In some arrangements, the ultrasonic transducer 12 is a circular disc shape. In this arrangement, the ultrasonic transducer 12 has a diameter of approximately 16 mm and a thickness of approximately 0.7 mm. In this arrangement, the ultrasonic transducer 12 is polarized to generate vibrations in the thickness mode.

In this arrangement, the ultrasonic transducer 12 is carried by a transducer holder 14 in the form of a ring which at least partly surrounds the ultrasonic transducer 12. In this arrangement, the transducer holder 14 is of silicone rubber. Apart from holding the ultrasonic transducer 12 in place, the transducer holder 14 also ensures minimal damping of the vibration of the ultrasonic transducer 12. In addition, the transducer holder 14 minimises the risk of the liquid ultrasonic wave transfer medium from leaking out from the base 10 of the cell lysis device 3.

In some arrangements, the ultrasonic transducer 12 is at least partly of a compound comprising lead, zirconium and titanium. The compound of the ultrasonic transducer 12 is selected to provide the ultrasonic transducer 12 with the properties for it to oscillate at a frequency of 2.8 MHz to 3.2 MHz. This frequency range is the preferred frequency range for the ultrasonic transducer 12 to produce ultrasonic waves which lyse or rupture cells.

In some arrangements, the ultrasonic transducer 12 comprises a first electrode on the upper side 13 and a second electrode on a lower side 15 which is on the opposing side of the ultrasonic transducer 12. In some arrangements, the first electrode and the second electrode comprise silver, for instance in the form of silver stamp paint. In some arrangements, the capacitance between the first electrode and the second electrode is 800 pF to 1300 pF.

In some arrangements, the first electrode on the upper side 13 of the ultrasonic transducer 12 is at least partly covered with a glass coating. The glass coating minimizes or prevents possible contamination of the ultrasonic wave transfer medium by the material of the first electrode. The glass coating also minimizes or prevents erosion of the silver of the first electrode, for instance due to cavitation bubble collapse caused by ultrasonic waves travelling through the ultrasonic wave transfer medium when the cell lysis device 3 is in use.

The first and second electrodes of the ultrasonic transducer 12 are connected electrically to respective first and second electrical terminals 16, 17 which are provided at the lower surface of the base 10 of the cell lysis device 3.

A plurality of projections 18, 19 (only two of which are visible in FIG. 2) extend outwardly from the side of the base 10 of the cell lysis device 3. The projections 18, 19 are part of the second interference fit attachment 5 of the cell lysis device 3. In other arrangement, the second interference fit attachment 5 comprises only one projection and in further arrangements, the second interference fit attachment 5 comprises more than 2 projections.

The cover 9 is provided at the opposite end of the cell lysis device 3 to the base 10. The cover 9 provides a generally planar circular surface and is formed integrally with the side wall 8 of the housing 7. In this arrangement, a bevelled edge 19 is provided around the circumference of the cover 9 at the intersection between the cover 9 and the side wall 8.

An opening 20 is provided in the cover 9. In this arrangement, the opening 20 is a generally circular aperture which is provided at the centre of the cover 9. In other arrangements, the opening 20 may be a different shape and may be provided in a different portion of the cover 9.

In this arrangement, a cylindrical collar 21 is aligned with the opening 20 and extends from the opening 20 into the sonication chamber 11. The opening 20 and the collar 21 are configured to receive a sample container 22 such that a part of the sample container 22 projects into the ultrasonic wave transfer medium within the sonication chamber 11.

In some arrangement, the sample container 22 is a microcentrifuge tube. In some arrangement, the sample container 22 is an Eppendorf Tube®. In some arrangements, the sample container 22 is a microcentrifuge tube or Eppendorf Tube® which holds a liquid volume of 0.5 ml, 1.5 ml or 2 ml.

The sample container 22 comprises a conical first portion 23 which is joined to a cylindrical body portion 24. A distal end of the body portion 24 is provided with a sample container aperture 24 through which a sample may be introduced into the sample container 22. A cap 25 is moveably mounted to the body portion 24, with the cap 25 being configured to seal the aperture 24 to retain a sample within the sample container 22.

The sample container 22 closes and seals the opening 20 when the sample container 22 is inserted into the opening 20. The housing 7 of the cell lysis device 3 is thus sealed to retain the ultrasonic wave transfer medium within the housing 7. In some arrangements, the sonication chamber 11 is initially empty and the sonication chamber 11 is filled with the ultrasonic wave transfer medium shortly before the sample container 22 is inserted into the opening 20.

Figure 4:
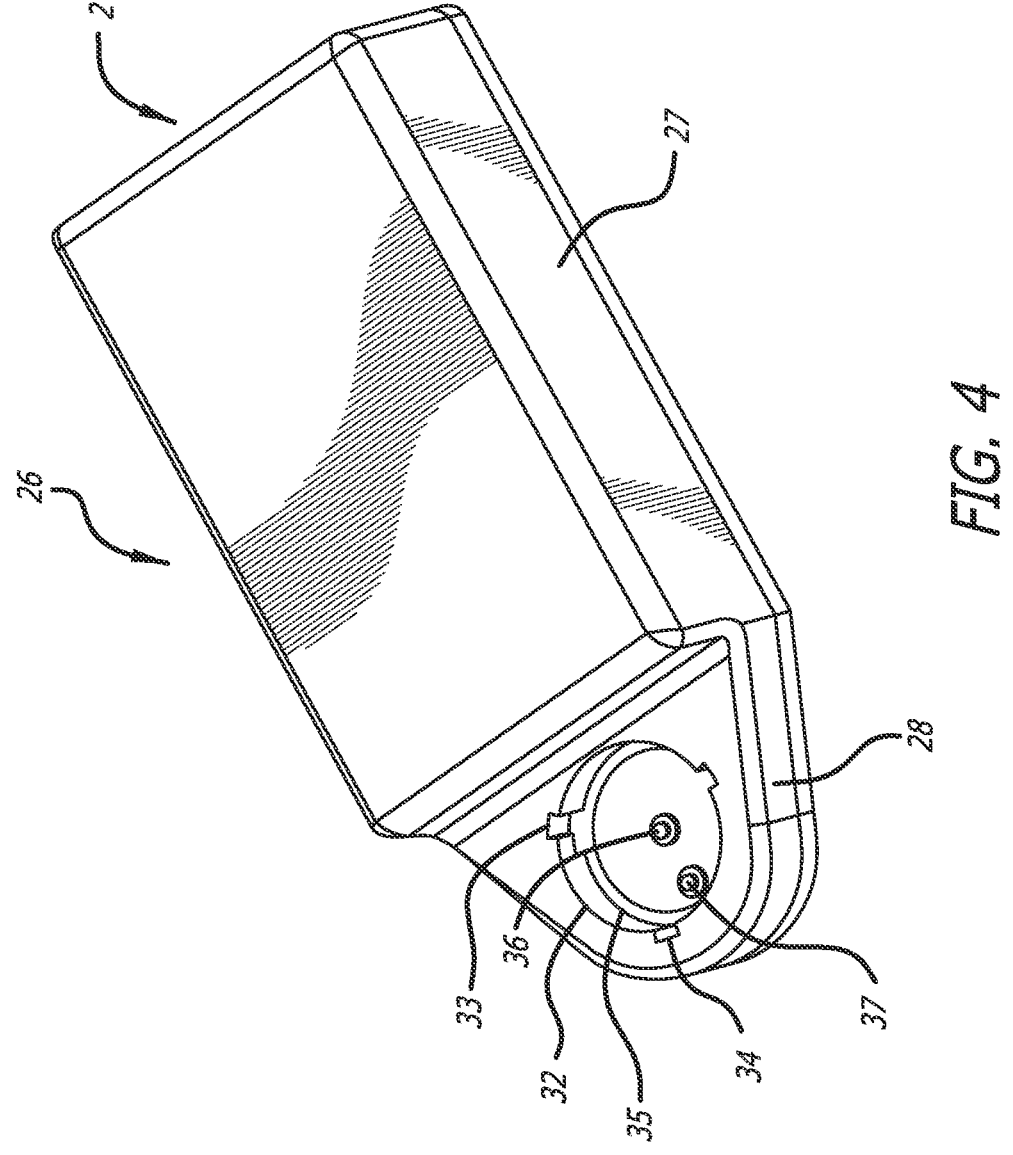
FIG. 4 is a diagrammatic perspective view of a driver apparatus of some arrangements.
Figure 5:
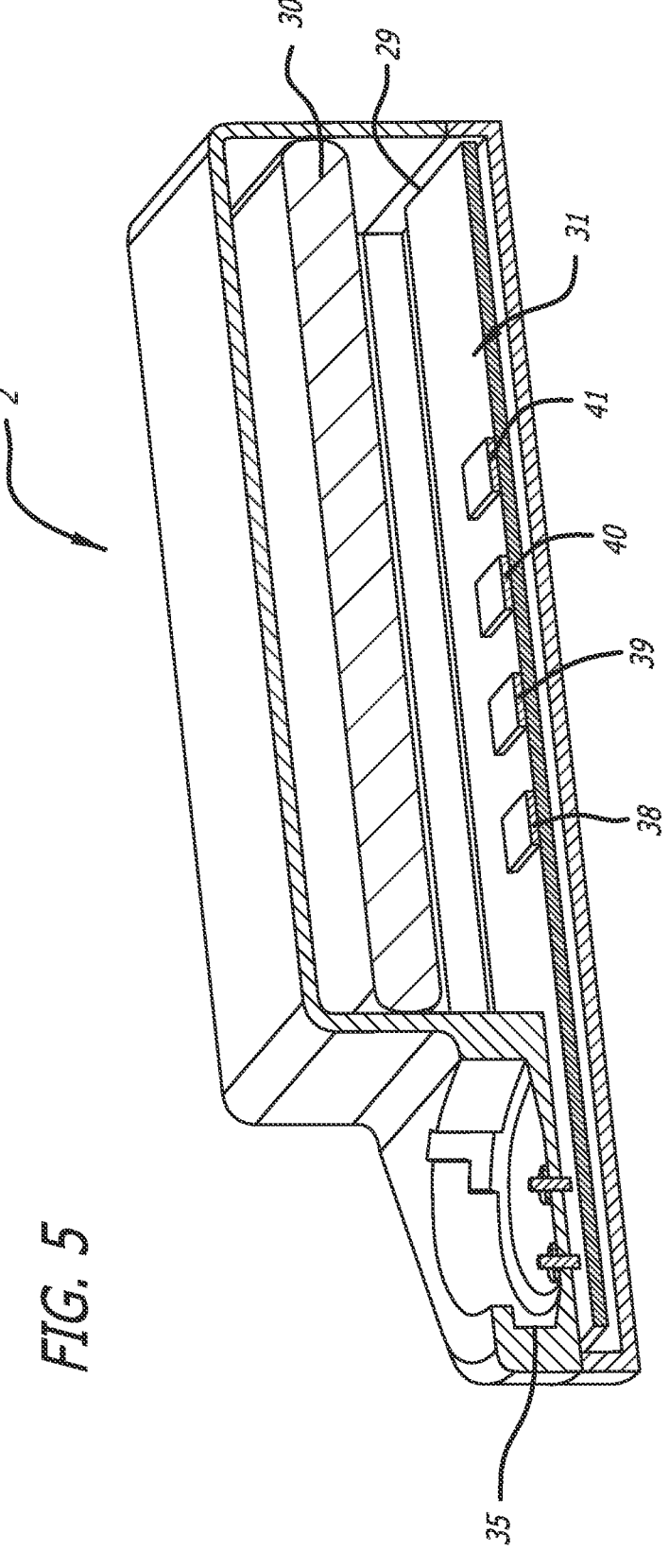
FIG. 5 is a cross-sectional view of the driver apparatus of FIG. 4.

Referring now to FIGS. 4 and 5 of the accompanying drawings, the driver apparatus 2 comprises a housing 26 which houses electrical components of the driver apparatus 2. In this arrangement, the driver apparatus 2 is a portable, stand-alone apparatus.

The housing 26 comprises a main housing 27 and a base protrusion 28. The main housing 27 comprises an internal chamber 29 which receives a battery 30 and at least part of a printed circuit board (PCB) 31. The PCB 31 carries the electronic components which provide the driver functionality of the driver apparatus 2.

In this arrangement, the battery 30 is rechargeable. In some arrangements, the battery 30 is a lithium polymer (LiPo) battery. In some arrangements, the capacity of the battery 30 provides sufficient power to enable the driver apparatus 2 to operate for at least 24 hours. In this arrangement, the driver apparatus 2 comprises a charging connection (not shown) which is configured to receive power from an external power source to charge the battery 30.

In some arrangements, the battery 30 is omitted and the driver apparatus 2 is instead provided with a power input connection to receive power from an external power source. In some arrangements, the external power source is a power adapter which converts a mains voltage to an appropriate voltage (e.g. 5-12V) to power the driver apparatus 2.

The base protrusion 28 is, in this embodiment, of reduced thickness compared with the housing 26. The base protrusion 28 is provided with a recess 32 which is configured to receive the base 10 of the cell lysis device 3. In this arrangement, the recess 32 is generally circular. The recess 32 is provided with indentations 33, 34 which are positioned above a generally circular channel 35 to form the first interference fit attachment 4 of the driver apparatus 2. The indentations 33, 34 are positioned to align with the projections 18, 19 on the cell lysis device 3. In other embodiments, there may be a different number of indentations which match a different number of projections on the cell lysis device 3.

Two driver output terminals 36, 37 are provided at the base of the recess 32. In this arrangement, one of the driver output terminals 36 is provided centrally within the recess 32 and the other driver output terminal 37 is provided adjacent the side of the recess 32. In this arrangement, each of the driver output terminals 36, 37 is a spring contact probe which protrudes upwardly from the base of the recess 32. The driver output terminals 36, 37 are positioned to engage and form an electrical connection with the first and second electrical terminals 16, 17 which are provided at the lower surface of the base 10 of the cell lysis device 3 when the cell lysis device 3 is attached to the driver apparatus 2. In some arrangements, the driver output terminals 36, 37 and/or the electrical terminals 16, 17 are of a brass material which is plated with a first 3 μm thick layer of nickel and a second 0.05 μm thick layer of gold.

In some arrangements, the driver output terminals 36, 37 extend through the base of the recess 32 to the PCB 31 where the driver output terminals 36, 37 are soldered to form an electrical connection with the PCB 31 and the electronic components provided on the PCB 31.

In this arrangement, the cell lysis device 3 is releasably attached to the driver apparatus 2 by placing the base 10 of the cell lysis device 3 into the recess 32 with the protrusions 18, 19 passing through the indentations 33, 34 until the protrusions 18, 19 are aligned with the channel 35. The cell lysis device 3 is then rotated with the protrusions 18, 19 within the channel 35. The protrusions 18, 19 are then retained within the channel 35 to provide an interference fit attachment which releasably attaches the cell lysis device 3 to the driver apparatus 2.

The interference fit attachments 4, 5 enable a user to releasably attach the cell lysis device 3 to the driver apparatus 2 by pushing and turning the cell lysis device 3 to lock the cell lysis device 3 to the driver apparatus. This process is then performed in reverse to remove the cell lysis device 3 from the driver apparatus 2 after the lysing process has finished.

As the cell lysis device 3 is pushed into the recess 32, the driver output terminals 36, 37 deform resiliently and align with the electrical terminals 16, 17 on the cell lysis device 3. The resiliently deformed driver output terminals 36, 37 press against the electrical terminals 16, 17 to form an electrical connection. When the cell lysis device 3 is releasably attached to the driver apparatus 2 in this way, the cell lysis device 3 is able to be driven by the driver apparatus 2 to lyse cells within the cell lysis device 3.

An AC driver 38 is provided on the PCB 31. The AC driver 38 generates an AC drive signal at a predetermined frequency and outputs the AC drive signal at the driver output terminals 36, 37 to drive the ultrasonic transducer 12 within the cell lysis device 3. In some arrangements, the AC driver 38 comprises a H-bridge circuit. In some arrangements, the H-bridge circuit comprises four MOSFETs which are connected to convert a direct current into an alternating current at high frequency (e.g. a frequency in the range 2.8 MHz to 3.2 MHz).

An active power monitoring arrangement 39 is provided on the PCB 31. The active power monitoring arrangement 39 monitors the active power used by the ultrasonic transducer 12 when the ultrasonic transducer 12 is driven by the AC drive signal. The active power monitoring arrangement 39 provides a monitoring signal which is indicative of an active power used by the ultrasonic transducer 12. In some arrangements, the active power monitoring arrangement 39 comprises a current sensing arrangement which senses a drive current of the AC drive signal driving the ultrasonic transducer 12 and provides a monitoring signal which is indicative of the sensed drive current.

The PCB 31 is provided with a processor 40 which controls the AC driver 38 and receives the monitoring signal from the active power monitoring arrangement 39. The PCB 31 is also provided with a memory 41 storing executable instructions for execution by the processor 40.

In some arrangements, the driver apparatus 2 comprises a frequency controller which is configured to control the frequency at which the ultrasonic transducer 12 operates. The frequency controller is implemented in the executable code stored in the memory 41 which, when executed by the processor 40, cause the processor 40 to perform at least one function of the frequency controller.

The memory 41 stores executable instructions which, when executed by the processor, cause the processor to control the ultrasonic transducer 12 to oscillate at a plurality of frequencies within a predetermined sweep frequency range and to select a drive frequency for the ultrasonic transducer 12 which is between a first predetermined frequency and a second predetermined frequency for lysing cells within the sample container 22.

In some arrangements, the frequency will be determined by the type of cells that are being lysed as some cells may require different frequencies due to their physical characteristics (size, shape, presence of cell wall, etc.).

There is an optimum frequency or frequency range for lysing cells. The optimum frequency or frequency range will depend on at least the following four parameters:

1. Transducer Manufacturing Processes

In some arrangements, the ultrasonic transducer 12 comprises a piezoelectric ceramic. The piezoelectric ceramic is manufactured by mixing compounds to make a ceramic dough and this mixing process may not be consistent throughout production. This inconsistency can give rise to a range of different resonant frequencies of the cured piezoelectric ceramic.

If the resonant frequency of the piezoelectric ceramic does not correspond to the required frequency of operation, the process of lysing cells is not optimal. Even a slight offset in the resonant frequency of the piezoelectric ceramic is enough to impact the lysing process, meaning that the system will not function optimally.

2. Load on Transducer

During operation, any changes in the load on the ultrasonic transducer 12 will inhibit the overall displacement of the oscillation of the ultrasonic transducer 12. To achieve optimal displacement of the oscillation of the ultrasonic transducer 12, the drive frequency must be adjusted to provide adequate power for maximum displacement.

The types of loads that can affect the efficiency of the ultrasonic transducer 12 can include the amount of liquid on the transducer (i.e. the amount of liquid within the sonication chamber 11).

3. Temperature

Ultrasonic oscillations of the ultrasonic transducer 12 are partially damped by its assembly in the driver apparatus 2. This dampening of the oscillations can cause a rise in local temperatures on and around the ultrasonic transducer 12.

An increase in temperature affects the oscillation of the ultrasonic transducer 12 due to changes in the molecular behaviour of the ultrasonic transducer 12. An increase in the temperature means more energy to the molecules of the ceramic, which temporarily affects its crystalline structure. Although the effect is reversed as the temperature reduces, a modulation in supplied frequency is required to maintain optimal oscillation.

An increase in temperature also reduces the viscosity of the solution within the sonication chamber 11, which may require an alteration to the drive frequency to optimise lysis of cells within the sonication chamber 11.

4. Distance to Power Source

The oscillation frequency of the ultrasonic transducer 12 can change depending on the wire-lengths between the ultrasonic transducer 12 and the AC driver 38. The frequency of the electronic circuit is inversely proportional to the distance between the ultrasonic transducer 49 and the controller 23.

Although the distance parameter is primarily fixed in this arrangement, it can vary during the manufacturing process of the system 1. Therefore, it is desirable to modify the drive frequency of the ultrasonic transducer 12 to compensate for the variations and optimise the efficiency of the system.

Figure 6:
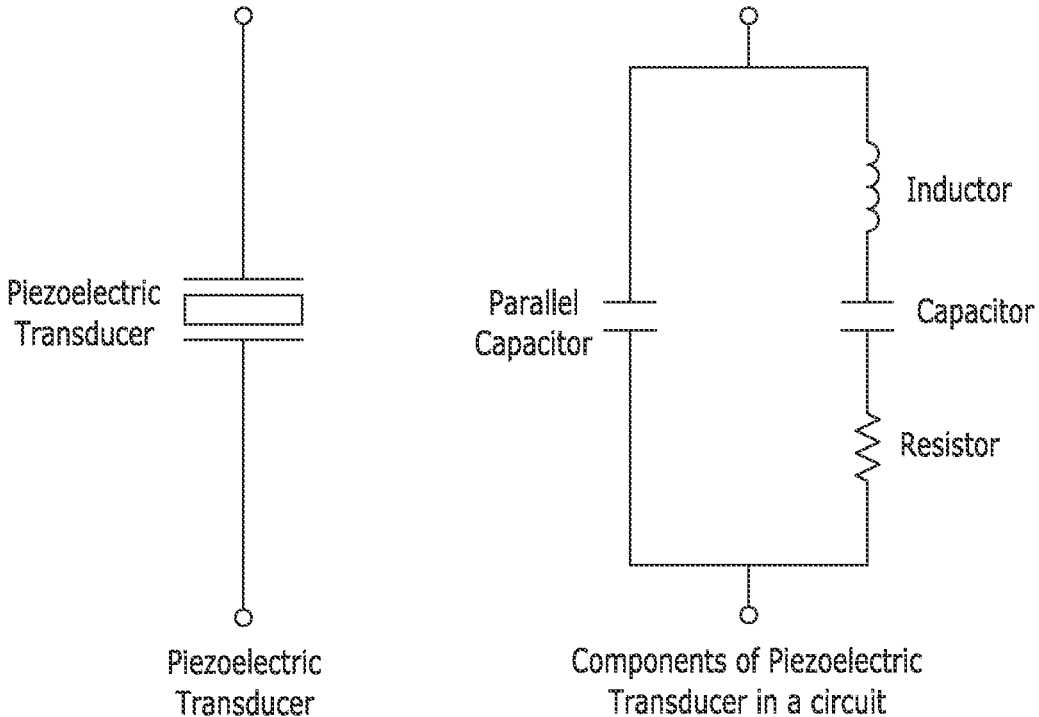
FIG. 6 is a diagram showing a piezoelectric transducer modelled as an RLC circuit.

A piezoelectric transducer can be modelled as an RLC circuit in an electronic circuit, as shown in FIG. 6. The four parameters described above may be modelled as alterations to the overall inductance, capacitance, and/or resistance of the RLC circuit, changing the resonance frequency range supplied to the transducer. As the frequency of the circuit increases to around the resonance point of the transducer, the log Impedance of the overall circuit dips to a minimum and then rises to a maximum before settling to a median range.

Figure 7:
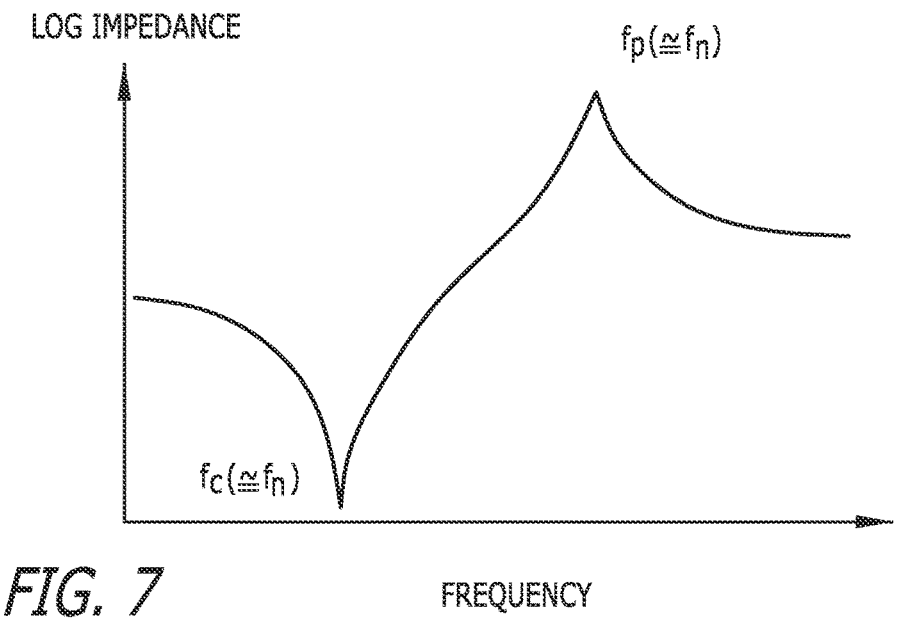
FIG. 7 is a graph showing the change in impedance with increase in frequency in an RLC circuit.
Figure 8:
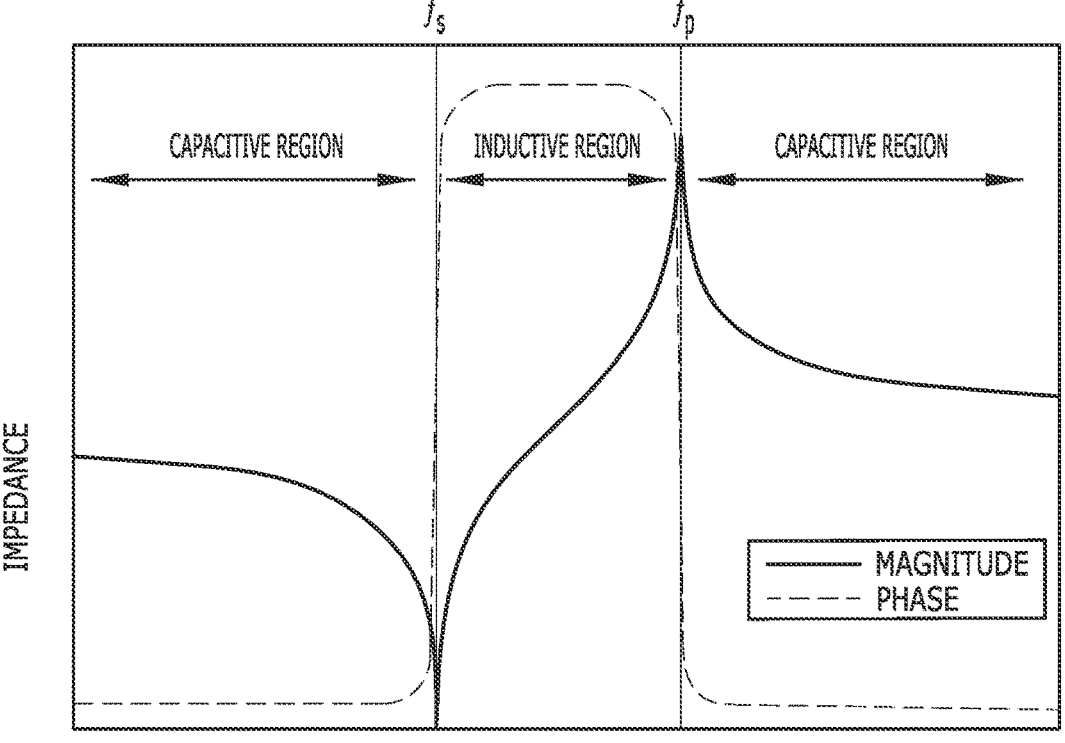
FIG. 8 is a graph showing how a piezoelectric transducer acts as a capacitor or an inductor.

FIG. 7 shows a graph explaining the change in overall impedance with increase in frequency in an RLC circuit. FIG. 8 shows how a piezoelectric transducer acts as a capacitor in a first capacitive region at frequencies below a first predetermined frequency $f_s$ and in a second capacitive region at frequencies above a second predetermined frequency $f_p$. The piezoelectric transducer acts as an inductor in an inductive region at frequencies between the first and second predetermined frequencies $f_s$, $f_p$. In order to maintain optimal oscillation of the transducer and hence maximum efficiency, the current flowing through the transducer must be maintained at a frequency within the inductive region.

The driver apparatus 2 of some arrangements is configured to maintain the frequency of oscillation of the piezoelectric transducer 12 within the inductive region, in order to maximise the efficiency of the lysis of cells.

The driver apparatus 2 is configured to perform a sweep operation in which the frequency controller drives the transducer at frequencies which track progressively across a predetermined sweep frequency range. In other words, the driver apparatus 2 drives the transducer at a plurality of different frequencies across the predetermined sweep frequency range. For instance at frequencies which increment by a predetermined frequency from one end of the sweep frequency range to the other end of the sweep frequency range.

As will be described in more detail below, the driver apparatus 2 of some arrangements determines the active power being used by the ultrasonic transducer 12 by monitoring the current flowing through the transducer 12.

Ultrasonic (piezoelectric) transducer mechanical deformation is linked to the AC Voltage amplitude that is applied to it, and in order to guarantee optimal functioning and delivery of the system, the maximum deformation must be supplied to the ultrasonic transducer all the time. By Pulse Width Modulation (PWM) of the AC voltage applied to the ultrasonic transducer, the mechanical amplitude of the vibration remains the same. In some arrangements, the system actively adjusts the duty cycle of the AC voltage waveform to maximise deformation of the ultrasonic transducer in order to guarantee optimal functioning and delivery of the system.

One approach involves modifying the AC voltage applied to the ultrasonic transducer via the use of a Digital to Analog Converter (DAC). The energy transmitted to the ultrasonic transducer would be reduced but so would the mechanical deformation which as a result does not produce maximum deformation. The RMS voltage applied to the ultrasonic transducer would be the same with effective Duty Cycle modulation as with Voltage modulation, but the active power transferred to the ultrasonic transducer would degrade. Indeed, given the formula below:

Active Power displayed to the ultrasonic transducer being:

$$Pa = \frac{2\sqrt{2}}{\pi} Irms * Vrms * \cos\varphi,$$

Where $\varphi$ is the shift in phase between current and voltage $I_{rms}$ is the root mean square Current $V_{rms}$ is the root mean square Voltage.

When considering the first harmonic, Irms is a function of the real voltage amplitude applied to the ultrasonic transducer, as the pulse width modulation alters the duration of voltage supplied to the ultrasonic transducer, controlling Irms.

In this arrangement, the memory 41 stores instructions which, when executed by the processor 40, cause the processor 40 to:

A. control the AC driver 38 to output an AC drive signal to the ultrasonic transducer 12 at a predetermined sweep frequency;

B. calculate the active power being used by the ultrasonic transducer 12 based on the monitoring signal;

C. control the AC driver 38 to modulate the AC drive signal to maximise the active power being used by the ultrasonic transducer 12;

D. store a record in the memory 41 of the maximum active power used by the ultrasonic transducer 12 and the sweep frequency of the AC drive signal;

E. repeat steps A-D for a predetermined number of iterations with the sweep frequency incrementing with each iteration such that, after the predetermined number of iterations has occurred, the sweep frequency has been incremented from a start sweep frequency to an end sweep frequency;

F. identify from the records stored in the memory 41 the optimum frequency for the AC drive signal which is the sweep frequency of the AC drive signal at which a maximum active power is used by the ultrasonic transducer 12; and G. control the AC driver 38 to output an AC drive signal to the ultrasonic transducer 12 at the optimum frequency.

In some arrangements, the start sweep frequency is 2800 kHz and the end sweep frequency is 3200 kHz. In other arrangements, the start sweep frequency and the end sweep frequency are lower and upper frequencies of a frequency range within the range of 2800 kHz to 3200 KHz.

In some arrangements, the processor 40 controls the AC driver 38 to output an AC drive signal to the ultrasonic transducer 12 at frequency which is shifted by between 1-10% of the optimum frequency. In these arrangements, the frequency shift is used to prolong the life of the ultrasonic transducer 12 by minimising potential damage caused to the ultrasonic transducer 12 when the ultrasonic transducer 12 is driven continuously at the optimum drive frequency which produces maximum displacement.

In some arrangements, the AC driver 38 modulates the AC drive signal by pulse width modulation to maximise the active power being used by the ultrasonic transducer 12.

In some arrangements, the processor 40 controls the AC driver 38 to alternately output an AC drive signal to the ultrasonic transducer 12 at the optimum frequency for a first predetermined length of time and to not output an AC drive signal to the ultrasonic transducer 12 for a second predetermined length of time. This alternate activation and deactivation of the ultrasonic transducer 12 has been found to optimise the process of lysing cells in a sample within the cell lysis device 3.

In some embodiments, in order to ensure optimal operation of the ultrasonic transducer 12, the driver apparatus 2 operates in a recursive mode. When the driver apparatus 2 operates in the recursive mode, the driver apparatus 2 runs the sweep of frequencies in steps A-D periodically during the operation of the system.

In some arrangements, the driver apparatus 2 activates automatically to start the lysing process when the cell lysis device 3 is attached to the driver apparatus 2. In some arrangements, the driver apparatus 2 stops the lysing process automatically after a predetermined length of time. Once the lysing process has finished, the cell lysis device 3 is removed from the driver apparatus 3.

In some arrangements, the processor 40 controls the AC driver 38 to alternately output the AC drive signal and to not output the AC drive signal according to an operating mode. The timings of twelve operating modes of some arrangements are shown in the table in FIG. 9 of the accompanying drawings.

In some arrangements, the driver apparatus 2 activates automatically when the cell lysis device 3 is attached to the driver apparatus 2. In other arrangements, the driver apparatus 2 is provided with a switch or other control device to enable a user to activate and deactivate the driver apparatus 2.

Once the system has been activated and has perfomed the lysing process for a predetermined duration, the cell lysis device 3 is separated from the driver apparatus 2. The liquid within the cell lysis device 3, which now contains lysed cells, is removed for use in another process, such as a PCR process. The cell lysis device 3 may then be discarded.

While the arrangements described above comprise one recess 32 and one set of driver output terminals 36, 37, other arrangements comprise a plurality of recesses and a plurality of sets of output terminals. In these other arrangments, the driver apparatus 2 can be used simultanously with a plurality of cell lysis devices. In these arrangements, the driver apparatus 2 controls each of the plurality of cell lysis devices to perform cell lysis individually.

The foregoing outlines features of several examples or embodiments so that those of ordinary skill in the art may better understand various aspects of the present disclosure. Those of ordinary skill in the art should appreciate that they may readily use the present disclosure as a basis for designing or modifying other processes and structures for carrying out the same purposes and/or achieving the same advantages of various examples or embodiments introduced herein. Those of ordinary skill in the art should also realise that such equivalent constructions do not depart from the spirit and scope of the present disclosure, and that they may make various changes, substitutions, and alterations herein without departing from the spirit and scope of the present disclosure.

Although the subject matter has been described in language specific to structural features or methodological acts, it is to be understood that the subject matter of the appended claims is not necessarily limited to the specific features or acts described above. Rather, the specific features and acts described above are disclosed as example forms of implementing at least some of the claims.

Various operations of examples or embodiments are provided herein. The order in which some or all of the operations are described should not be construed to imply that these operations are necessarily order dependent. Alternative ordering will be appreciated having the benefit of this description. Further, it will be understood that not all operations are necessarily present in each embodiment provided herein. Also, it will be understood that not all operations are necessary in some examples or embodiments.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application and the appended claims are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising". Also, unless specified otherwise, "first," "second," or the like are not intended to imply a temporal aspect, a spatial aspect, an ordering, etc. Rather, such terms are merely used as identifiers, names, etc. for features, elements, items, etc. For example, a first element and a second element generally correspond to element A and element B or two different or two identical elements or the same element.

Also, although the disclosure has been shown and described with respect to one or more implementations, equivalent alterations and modifications will occur to others of ordinary skill in the art based upon a reading and understanding of this specification and the annexed drawings. The disclosure comprises all such modifications and alterations and is limited only by the scope of the following claims. In particular regard to the various functions performed by the above described features (e.g., elements, resources, etc.), the terms used to describe such features are intended to correspond, unless otherwise indicated, to any features which performs the specified function of the described features (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

Examples or embodiments of the subject matter and the functional operations described herein can be implemented in digital electronic circuitry, or in computer software, firmware, or hardware, including the structures disclosed in this specification and their structural equivalents, or in combinations of one or more of them.

Some examples or embodiments are implemented using one or more modules of computer program instructions encoded on a computer-readable medium for execution by, or to control the operation of, a data processing apparatus. The computer-readable medium can be a manufactured product, such as hard drive in a computer system or an embedded system. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The terms "computing device" and "data processing apparatus" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment, or a combination of one or more of them. In addition, the apparatus can employ various different computing model infrastructures, such as web services, distributed computing and grid computing infrastructures.

The processes and logic flows described in this specification can be performed by one or more programmable processors executing one or more computer programs to perform functions by operating on input data and generating output.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices.

In the present specification "comprise" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. A cell lysis system comprising:

a sample container configured to contain a sample of cells, the sample container including a tube having an interior space and a closed lower end for holding the sample of cells within the interior space, the sample of cells being in a liquid solution which is fully contained in the interior space within the sample container;

a sonication capsule including:

a housing having a side wall, a base and a cover opposite to the base, the cover including an opening which receives at least a part of the tube of the sample container, the at least a part of the tube of the sample container closing and sealing the opening in the cover;

a sonication chamber provided within the housing, the sonication chamber being at least partly filled with an ultrasonic wave transfer medium, the ultrasonic wave transfer medium being a liquid having an acoustic impedance, wherein the sample container projects into the ultrasonic wave transfer medium and the ultrasonic wave transfer medium is retained within the sonication chamber by the part of the tube of the sample container which closes and seals the opening in the cover of the housing, the sample container containing the sample of cells in the liquid solution within the interior space of the sample container separate from the ultrasonic wave transfer medium present in the sonication chamber;

an ultrasonic transducer within the sonication chamber positioned at the closed lower end of the sample container, the ultrasonic transducer being in contact with the ultrasonic wave transfer medium in the sonication chamber and outside of the sample container, the ultrasonic transducer not contacting the liquid solution with the sample of cells contained within the sample container;

a plurality of electrical terminals connected electrically to the ultrasonic transducer; and a driver apparatus, the sonication capsule being releasably attached to the driver apparatus, the driver apparatus including:

a plurality of driver output terminals which are connected electrically to the plurality of electrical terminals of the sonication capsule to provide an electrical connection between the driver apparatus and the sonication capsule to drive the ultrasonic transducer within the sonication capsule;

an AC driver which generates an AC drive signal at a predetermined frequency and outputs the AC drive signal at the driver output terminals to drive the ultrasonic transducer within the sonication capsule;

an active power monitoring arrangement which monitors the active power used by the ultrasonic transducer when the ultrasonic transducer is driven by the AC drive signal, wherein the active power monitoring arrangement provides a monitoring signal which is indicative of an active power used by the ultrasonic transducer;

a processor which controls the AC driver and receives the monitoring signal from the active power monitoring arrangement; and a memory storing instructions which, when executed by the processor, cause the processor to:

A. control the AC driver to output an AC drive signal to the ultrasonic transducer at a predetermined sweep frequency;

B. calculate the active power being used by the ultrasonic transducer based on the monitoring signal;

C. control the AC driver to modulate the AC drive signal to maximize the active power being used by the ultrasonic transducer;

D. store a record in the memory of the maximum active power used by the ultrasonic transducer and the sweep frequency of the AC drive signal;

E. repeat steps A-D for a predetermined number of iterations with the sweep frequency incrementing with each iteration such that, after the predetermined number of iterations has occurred, the sweep frequency has been incremented from a start sweep frequency to an end sweep frequency;

F. identify from the records stored in the memory the optimum frequency for the AC drive signal which is the sweep frequency of the AC drive signal at which a maximum active power is used by the ultrasonic transducer; and G. control the AC driver to activate the ultrasonic transducer for a first predetermined length of time, deactivate the ultrasonic transducer for a second predetermined length of time and activate the ultrasonic transducer for a third predetermined length of time to alternately output an AC drive signal to the ultrasonic transducer at the optimum frequency when the ultrasonic transducer is activated and not output the AC drive signal to the ultrasonic transducer when the ultrasonic transducer is deactivated, the ultrasonic transducer generating ultrasonic waves in the ultrasonic wave transfer medium within the sonication chamber when the ultrasonic transducer is activated, the ultrasonic waves being transferred by the ultrasonic wave transfer medium from the ultrasonic transducer to the sample container to lyse the sample of cells in the liquid solution contained within the sample container, the lysed sample of cells remaining within the sample container and the liquid solution with the lysed sample of cells not being in contact with the ultrasonic transducer.

2. The system of claim 1, wherein the active power monitoring arrangement comprises:

a current sensing arrangement which senses a drive current of the AC drive signal driving the ultrasonic transducer, wherein the active power monitoring arrangement provides a monitoring signal which is indicative of the sensed drive current.

3. The system of claim 1, wherein the memory stores instructions which, when executed by the processor, cause the processor to:

repeat steps A-D with the sweep frequency being incremented from a start sweep frequency of 2800 kHz to an end sweep frequency of 3200 kHz.

4. The system of claim 1, wherein the memory stores instructions which, when executed by the processor, cause the processor to:

in step G, when activating the ultrasonic transducer, control the AC driver to output an AC drive signal to the ultrasonic transducer at a frequency which is shifted by between 1-10% of the optimum frequency.

5. The system of claim 1, wherein the AC driver modulates the AC drive signal by pulse width modulation to maximise the active power being used by the ultrasonic transducer.

6. The system of claim 1, wherein the memory stores instructions which, when executed by the processor, cause the processor to:

alternately output the AC drive signal when the ultrasonic transducer is activated and to not output the AC drive signal when the ultrasonic transducer is deactivated according to an operating mode selected from:

| Operating mode | First predetermined length of time (seconds) | Second predetermined length of time (seconds) |
|---|---|---|
| 1 | 4 | 2 |
| 2 | 3 | 2 |
| 3 | 2 | 2 |
| 4 | 1 | 2 |
| 5 | 1 | 1 |
| 6 | 2 | 1 |
| 7 | 3 | 1 |
| 8 | 4 | 1 |
| 9 | 4 | 3 |
| 10 | 3 | 3 |
| 11 | 2 | 3 |
| 12 | 1 | 3 |

7. The system of claim 1, wherein the driver apparatus comprises a first interference fit attachment and the sonication capsule comprises a second interference fit attachment, and wherein the first interference fit attachment releasably attaches to the second interference fit attachment to releasably attach the sonication capsule to the driver apparatus.

8. The system of claim 1, wherein the cell lysis device further comprises a transducer holder which is coupled to the base of the housing, the transducer holder carrying and at least partly surrounding the ultrasonic transducer.

9. The system of claim 1, wherein the ultrasonic wave transfer medium is a liquid which has a higher acoustic impedance than water.

10. The system of claim 1, wherein the ultrasonic wave transfer medium is vegetable glycerine.

11. The system of claim 1, wherein the housing of the sonication capsule is cylindrical, the base of the sonication capsule is generally circular and positioned at a first end of the sonication capsule and the cover of the sonication capsule is circular and positioned at a second end of the sonication capsule opposite to the first end of the sonication capsule.

12. The system of claim 1, wherein the sonication capsule is a disposable, single-use capsule.

13. The system of claim 1, wherein the sonication chamber is pre-filled with the ultrasonic wave transfer medium.

* * * * *